United States Patent [19]

Reno

[11] 4,064,871

[45] Dec. 27, 1977

[54] DEVICE FOR MAKING PRECISE INCISIONS FOR BLEEDING TIME TESTING AND THE LIKE

[75] Inventor: Woodrow James Reno, Baltimore, Md.

[73] Assignee: Becton, Dickinson and Company, East Rutherford, N.Y.

[21] Appl. No.: 685,370

[22] Filed: May 11, 1976

[51] Int. Cl.² .............................................. A61B 10/00
[52] U.S. Cl. .................................. 128/2 G; 30/272 R; 128/314
[58] Field of Search ................ 128/2 G, 305, 314; 30/272 R

[56] References Cited

U.S. PATENT DOCUMENTS

| 2,711,738 | 6/1955 | Kelly et al. | 128/314 |
|---|---|---|---|
| 2,823,677 | 2/1958 | Hein, Jr. | 128/314 |
| 3,712,293 | 1/1973 | Mielke, Jr. | 128/2 G |
| 3,760,809 | 9/1973 | Campbell, Jr. | 128/314 |
| 3,902,475 | 9/1975 | Begg et al. | 128/2 G X |

Primary Examiner—Kyle L. Howell
Attorney, Agent, or Firm—Kane, Dalsimer, Kane, Sullivan and Kurucz

[57] ABSTRACT

A device for making a standardized reproducible blade incision in a human or animal subject for clinically testing the bleeding time of the subject is provided. The device comprises a housing having a surface with a slot defining a longitudinal opening into the housing. A blade is mounted within the housing for movement of the blade tip through and along the slot. Biasing springs are provided within the housing to urge the blade through the slot a predetermined distance and along the slot for a predetermined length to control the depth and length of an incision produced with the device. A trigger is provided to initiate movement of the blade along with a safety pin to prevent the inadvertent activation of the device.

5 Claims, 7 Drawing Figures

DEVICE FOR MAKING PRECISE INCISIONS FOR BLEEDING TIME TESTING AND THE LIKE

BACKGROUND OF THE INVENTION

As is well known, when a human or animal subject suffers a cut or injury causing bleeding, in due course blood flowing from the wound coagulates and bleeding ceases. At this time hemostasis is completed and no further blood flows from the wound. The time during which blood flows is known as the "bleeding time" and, for most people, this occurs for a normal time period.

It is often necessary, as for example when surgery is contemplated, to determine if the patient suffers from a disorder or the effects of medication which may abnormally affect the patient's bleeding time. To this end, in order to test the bleeding time, it is necessary to form a reproducible incision on the patient, usually on the patient's forearm and to measure the time required for bleeding to cease. The test may be repeated after a period of time to check for improvement or deterioration and in this connection, it is imperative that the incision formed be of the same length and depth as the previous test incision.

In view of the above, it is the principal object of the present invention to provide a simple, automatic device capable of producing and reproducing incisions of precise length and depth to facilitate such bleeding time testing.

A further object is to provide such a device which may be readily triggered to form the desired incision but which, prior to use, may be safely handled and stored without danger of the device being accidentally triggered.

SUMMARY OF THE INVENTION

The above and other beneficial objects and advantages are attained in accordance with the present invention by providing a device for the formation of precise incisions for clinically testing the bleeding time of human or animal subjects. The device comprises a housing having a surface with a slot defining a longitudinal opening into the housing. A blade is mounted within the housing for movement of the blade tip through and along the slot. Biasing springs are provided within the housing to urge the blade through the slot a predetermined distance and along the slot for a predetermined length to control the depth and length of an incision produced with the device. A trigger is provided to initiate movement of the blade along with a safety pin to prevent the inadvertent activation of the device.

DETAILED DESCRIPTION OF THE PREFERRED EMBODIMENT

Figure 1:
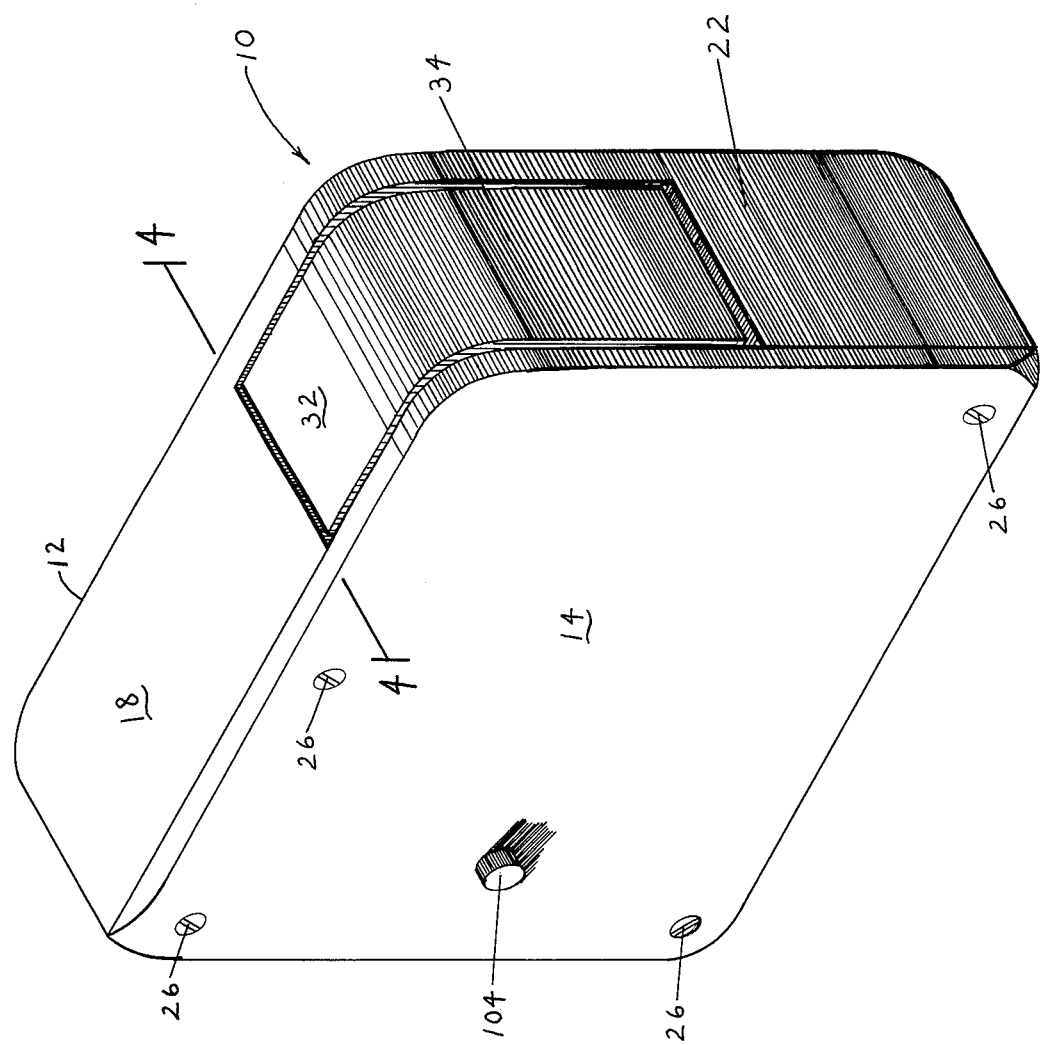
FIG. 1 is a perspective view of a device for the formation of precise incisions in accordance with the present invention.
Figure 4:
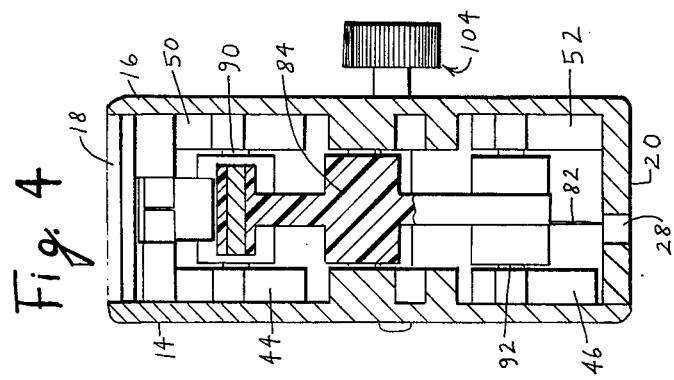
FIG. 4 is an end elevational view partly in section depicting the arrangement of the components.

Reference is now made to the drawings wherein the incision forming device of the present invention is shown. Referring to FIG. 1, it can be seen that the device 10 comprises a generally rectangular housing 12 having front and rear surfaces defined respectively by plates 14 and 16, top and bottom surfaces 18 and 20, and side surfaces 22 and 24. With the exception of plate 14, the remainder of the housing is formed integrally with plate 14 secured to the remainder of the housing by screws 26.

As shown, the interior of the housing is hollow and a slot 28 extends through the bottom surface defining an opening into the housing interior. A second opening 30 extends between the upper part of side surface 22 and the forward part of top surface 18. This opening is filled by the trigger member 32 which is contoured to conform to the remainder of the housing to substantially fill the entire opening. Trigger member 32 is J-shaped in side elevation with the stem 34 of member 32 resiliently mounted to surface 22 by a leaf spring 36 secured by rivets 38 to both the trigger member and housing.

Figure 3:
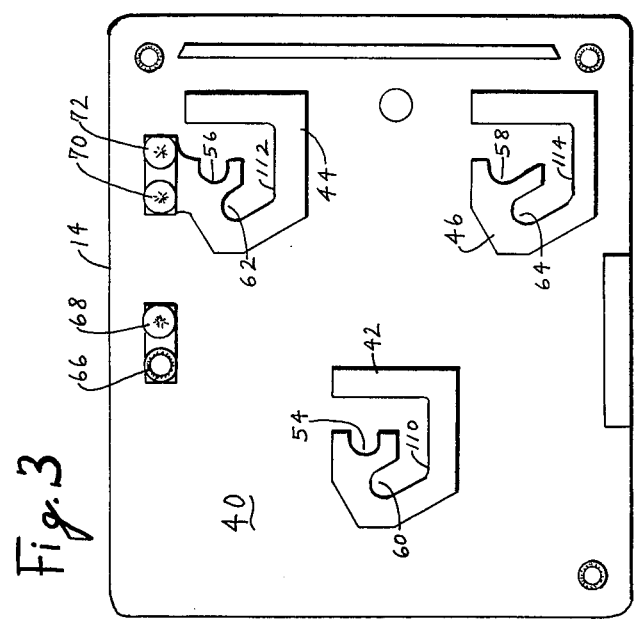
FIG. 3 is a side elevational view of the interior surface of the cover plate depicting camming guides integrally formed thereon.

The interior surfaces of plates 14 and 16 are substantially mirror images of each other and provided with a series of integrally formed camming guide surfaces. Accordingly, the inner surface 40 of plate 14 includes camming guides 42, 44 and 46 which are positioned in the assembled unit opposite camming guides 48, 50 and 52 respectively which are integrally formed on the inner surface of plate 16. Each of the camming guides includes a first, upper position designated by the numerals 54, 56 and 58 and a second position as shown in FIG. 3 and designated by the numerals 60, 62 and 64 respectively on camming guides 42, 44 and 46. As stated, camming guides 48, 50 and 52 on the interior surface of plate 16 are identical with the guides on the interior of plate 14 and include corresponding first and second positions which register with the corresponding guides of plate 14. In addition, the interior surface of plate 14 is provided with a first series of pins 66 and 68 and a second series of pins 70 and 72 about which springs are disposed in a manner to be described forthwith. Corresponding posts 74, 76, 78 and 80 are provided on the interior of plate 16.

The blade 82 with which incisions are formed is mounted to a block 84 disposed within the housing. In this connection, the blade is secured with a single screw 86 enabling it to be easily replaced as required. Alternately, if desired, the entire unit can be manufactured of relatively inexpensive materials so as to be disposable after a single use or block 84 and a mounted blade could be replaced as a single unit after use. The sharpened tip 88 of the blade is directed toward the slot 28 as shown.

The mounting block 84 is provided with three integral cam followers 90, 92 and 94 each comprising a post extending transversely from both sides of the block. Thus, the ends of post 90 are designed to ride in cam guide 44 on plate 14 and its associated guide 50 on plate 16; the ends of post 94 ride in guide 42 and its associated guide 48; and, similarly, the ends of post 92 ride in guide 46 and its associated guide 52.

Figure 2:
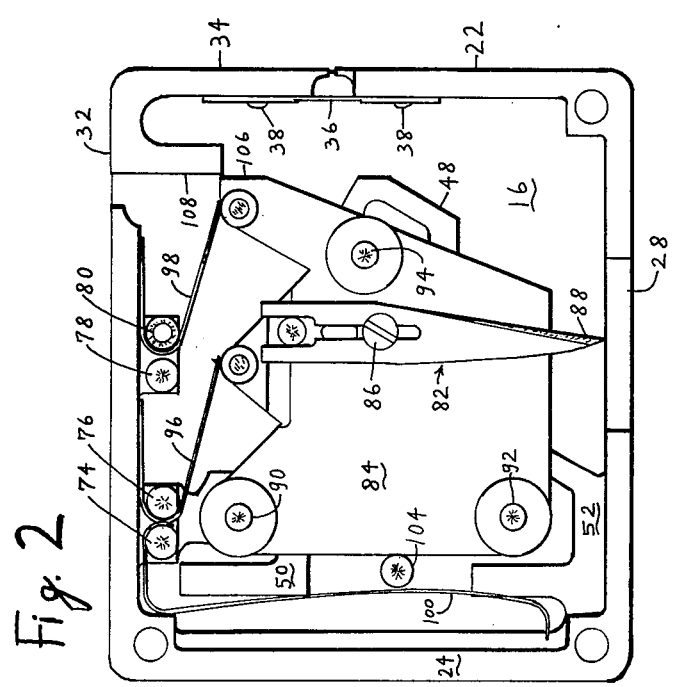
FIG. 2 is a side elevational view of the device of FIG. 1 with the cover plate removed to disclose the interior of the device.

A pair of springs 96 and 98 extend about posts 76 and 80 as shown in FIGS. 2 and 5-7 and are biased to urge the block 84 downwardly so as to direct the blade tip 88 through slot 28. A further spring 100 extends about post 74 and is biased to exert a horizontally directed force against block 84. In this connection, a hole 102 is provided in surface 16 of the casing and a safety pin 104 is inserted through the opening (as shown in FIG. 2) to prevent spring 100 from engaging block 84. Pin 104 also prevents the horizontal movement of the block in a manner to be described forthwith.

The unarmed condition of the device 10 is shown in FIG. 2. In this condition, each of the camming posts 94, 90 and 92 is in the upper portion (i.e., 54, 56 and 58 respectively) of camming guides 42, 44 and 46 of plate 14 and the corresponding portions of guides of plate 16. In this position the block 84 is raised so that the tip 88 of blade 82 does not extend through the slot. The upper forward edge generally designated by the numeral 106 engages the turned in lip 108 of the inverted J-shaped trigger member 34 thereby preventing movement of the block. It should be noted that with pin 104 in position, even if the trigger is pushed inwardly, pin 104 locks the block in position thereby preventing the camming posts from moving horizontally out of the upper positions of the associated camming guides.

Figure 5:
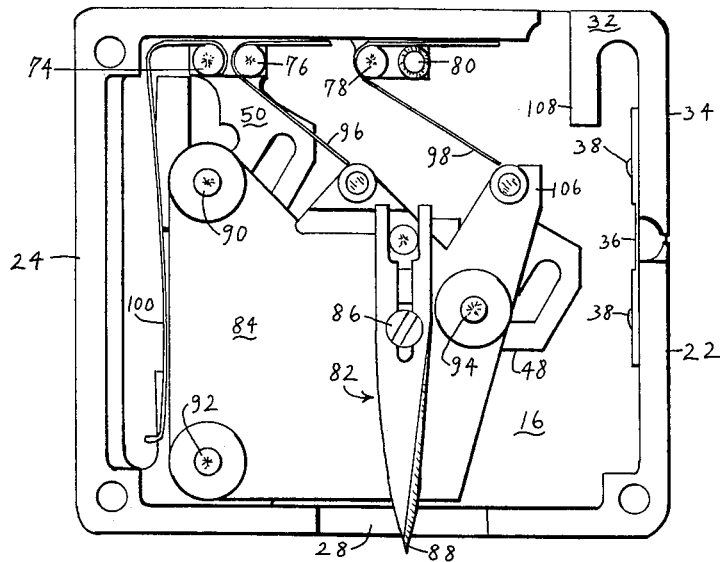
FIG. 5 is a view similar to FIG. 2 depicting the interior of the housing with the safety pin removed immediately after the triggering mechanism has been fired and the blade urged downwardly.
Figure 6:
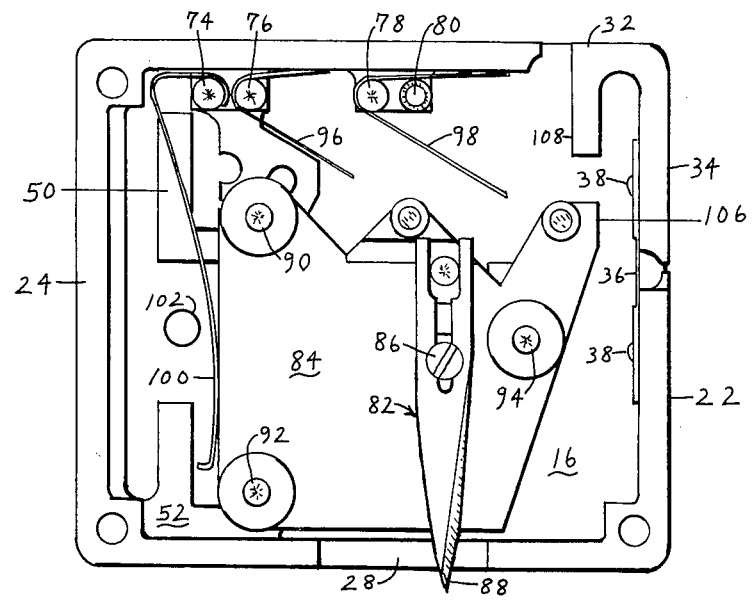
FIG. 6 is a view similar to FIG. 5 depicting the components within the interior of the housing as the blade is urged forward longitudinally; and, FIG. 7 is a view similar to FIG. 6 depicting the interior of the housing after the blade has completed its movement and is returned to an inert position.
Figure 7:
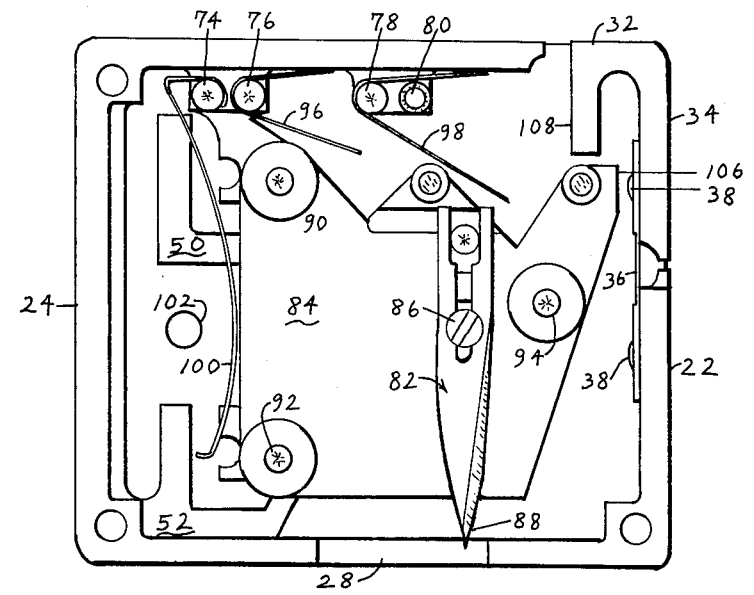

When pin 104 is removed the device is armed and ready to be fired. Upon removal of pin 104, spring 100 shifts to a position abutting block 84 as shown in FIG. 5. However, the lip 108 of the trigger 32 prevents any further movement of the block by virtue of the block upper forward edge 106 hanging on to the lip. When the trigger is depressed, the lip 108 rotates out of the path of movement of the block, thus allowing springs 96 and 98 to urge the block downwardly so that the tip 88 of blade 82 extends through slot 28 as shown in FIG. 5. The block is then moved horizontally under the action of spring 100 as shown in FIG. 6. During this time, the cam followers move along the horizontal portions 110, 112 and 114 respectively of guides 42, 44 and 46 and the corresponding portions of guides 48, 50 and 52. These portions terminate in the upwardly tapered portions 60, 62 and 64 respectively which move block 84 upwardly and thus withdraw the blade from the slot after the blade traverses the length of the slot as shown in FIG. 7.

In operation, the device is placed against a subject with the slot making contact with the patient's skin. After arming the device by removing pin 104, the technician depresses trigger 32 after the device is in position. As a result, the blade automatically extends through and across the slot as described above, in conjunction with FIGS. 5, 6 and 7, thereby producing an incision of predetermined depth and length.

Thus, in accordance with the above, the aforementioned objects are effectively attained.

Having thus described the invention, what is claimed is:

1. A device for the formation of precise incisions for clinically testing the bleeding time of human or animal subjects comprising: a housing; a surface on said housing; a slot extending along said surface defining a longitudinal opening into said housing; a blade mounted for movement within said housing, said blade having a tip end directed toward said slot; and, moving means mounted within said housing and operationally engaging said blade to move said blade (1) a predetermined distance through said slot and (2) a predetermined distance along said slot.

2. The device in accordance with claim 1 wherein said blade is mounted to a block within said housing, said block includes camming surfaces thereon for following camming guides in said housing; said moving means comprises spring means biased against said block to urge said block camming surfaces along said camming guides; and further comprising a trigger having portions within said housing shiftable from a position engaging said block and preventing said block from moving to a position out of contact with said block.

3. The device in accordance with claim 2 wherein said spring means includes a first spring to move said block through said slot and a second spring to move said blade along said slot.

4. The device in accordance with claim 2 wherein said blade is removably mounted to said block.

5. The device in accordance with claim 2 further comprising safety pin means removably extending through said housing interposed between said spring means and said block whereby to lock said block in position and prevent said spring means from acting upon said block.

* * * * *